US00PP24214P2

(12) United States Plant Patent
Jacobs

(10) Patent No.: US PP24,214 P2
(45) Date of Patent: Feb. 4, 2014

(54) ***ALSTROEMERIA* PLANT NAMED 'ZAPRIKATE'**

(50) Latin Name: *Alstroemeria hybrida*
Varietal Denomination: Zaprikate

(75) Inventor: Henricus Cornelius Maria Jacobs, EW Rijsenhout (NL)

(73) Assignee: Van Zanten Plants b.v., Hillegom (NL)

( * ) Notice: Subject to any disclaimer, the term of this patent is extended or adjusted under 35 U.S.C. 154(b) by 62 days.

(21) Appl. No.: 13/506,952

(22) Filed: May 25, 2012

(51) Int. Cl.
*A01H 5/00* (2006.01)

(52) U.S. Cl.
USPC ..... Plt./309

(58) Field of Classification Search
USPC ..... Plt./309
See application file for complete search history.

*Primary Examiner* — Annette Para
(74) *Attorney, Agent, or Firm* — C. A. Whealy

(57) ABSTRACT

A new and distinct cultivar of *Alstroemeria* plant named 'Zaprikate', characterized by its compact, upright, somewhat outwardly spreading and uniformly mounded plant habit; vigorous growth habit; bright red-colored flowers; and excellent container and garden performance.

1 Drawing Sheet

Botanical designation: *Alstroemeria hybrida.*
Cultivar denomination: 'ZAPRIKATE'.

BACKGROUND OF THE INVENTION

The present invention relates to a new and distinct cultivar of *Alstroemeria* plant, botanically known as *Alstroemeria hybrida*, commercially used as a potted and garden-type *Alstroemeria* plant and hereinafter referred to by the name 'Zaprikate'.

The new *Alstroemeria* plant is a product of a planned breeding program conducted by the Inventor in Rijsenhout, The Netherlands. The objective of the breeding program is to create new potted *Alstroemeria* plants with uniform plant habit, freely flowering habit, attractive foliage and flower coloration and good garden performance.

The new *Alstroemeria* plant originated from a cross-pollination made by the Inventor in Rijsenhout, The Netherlands in July, 2007, of a proprietary *Alstroemeria hybrida* selection identified as code number 5779-1, not patented, as the female, or seed, parent with a proprietary *Alstroemeria hybrida* selection identified as code number 66480-1, not patented, as the male, or pollen, parent. The new *Alstroemeria* plant was discovered and selected by the Inventor as a single flowering plant from within the progeny of the stated cross-pollination in a controlled greenhouse environment in Rijsenhout, The Netherlands in August, 2008.

Asexual reproduction of the new *Alstroemeria* plant by rhizome divisions in a controlled greenhouse environment in Rijsenhout, The Netherlands since September, 2008 has shown that the unique features of this new *Alstroemeria* plant are stable and reproduced true to type in successive generations.

SUMMARY OF THE INVENTION

Plants of the new *Alstroemeria* have not been observed under all possible environmental conditions and cultural conditions. The phenotype may vary somewhat with variations in environmental conditions such as temperature and light intensity without, however, any variance in genotype.

The following traits have been repeatedly observed and are determined to be the unique characteristics of 'Zaprikate'. These characteristics in combination distinguish 'Zaprikate' as a new and distinct *Alstroemeria* plant:

1. Compact, upright, somewhat outwardly spreading and uniformly mounded plant habit.
2. Vigorous growth habit.
3. Bright red-colored flowers.
4. Excellent container and garden performance.

Plants of the new *Alstroemeria* differ primarily from plants of the female parent selection in flower color as plants of the female parent selection have darker red-colored flowers.

Plants of the new *Alstroemeria* differ primarily from plants of the male parent selection in plant habit as plants of the new *Alstroemeria* are more compact than plants of the male parent selection.

Plants of the new *Alstroemeria* can be compared to plants of *Alstroemeria hybrida* 'Staprioxa', disclosed in U.S. Plant Pat. No. 14,075. In side-by-side comparisons conducted in Rijsenhout, The Netherlands, plants of the new *Alstroemeria* differed primarily from plants of 'Staprioxa' in the following characteristics:

1. Plants of the new *Alstroemeria* were more compact than plants of 'Staprioxa'.
2. Plants of the new *Alstroemeria* had slightly larger flowers than plants of 'Staprioxa'.
3. Plants of the new *Alstroemeria* and 'Staprioxa' differed in flower color as plants of 'Staprioxa' had red purple-colored flowers.

BRIEF DESCRIPTION OF THE PHOTOGRAPH

The accompanying colored photograph illustrates the overall appearance of the new *Alstroemeria* plant showing the colors as true as it is reasonably possible to obtain in colored reproductions of this type. Colors in the photograph may differ slightly from the color values cited in the detailed botanical description which accurately describe the colors of the new *Alstroemeria* plant. The photograph comprises a side perspective view of a typical flowering plant of 'Zaprikate' grown in a ground bed.

DETAILED BOTANICAL DESCRIPTION

The aforementioned photograph and following observations and measurements describe plants of the new *Alstroemeria* grown during the late summer in ground beds in a glass-covered greenhouse in Rijsenhout, The Netherlands. During the production of the plants, day temperatures ranged from 15° C. to 25° C., night temperatures ranged from 10° C. to 15° C. and light levels averaged 5,000 lux. Plants were six months old when the photograph and the description were taken. In the following description, color references are made to The Royal Horticultural Society Colour Chart, 2007 Edition, except where general terms of ordinary dictionary significance are used.

Botanical classification: *Alstroemeria hybrida* 'Zaprikate'.

Parentage:

*Female, or seed, parent*.—Proprietary *Alstroemeria hybrida* selection identified as code number 5779-1, not patented.

*Male or pollen parent*.—Proprietary *Alstroemeria hybrida* selection identified as code number 66480-1, not patented.

Propagation:

*Type*.—In vitro rhizogenesis.

*Time to produce a rooted young plant, summer*.—About 40 days.

*Time to produce a rooted young plant, winter*.—About 60 days.

*Root description*.—Fibrous, fleshy, thick; close to 155D in color.

*Rooting habit*.—Freely branching; medium density.

*Rhizomes*.—Shape: Elongate; rounded. Length: About 10 cm to 30 cm. Diameter: About 3 mm to 10 mm. Texture: Smooth. Color: Close to 155D.

Plant description:

*Plant and growth habit*.—Compact, upright, somewhat outwardly spreading and uniformly mounding plant habit; freely branching habit, dense and bushy appearance; vigorous growth habit.

*Plant height*.—About 14 cm to 22 cm.

*Plant diameter* (*spread*).—About 25 cm to 35 cm.

Lateral branch description:

*Aspect*.—Mostly upright.

*Length*.—About 7 cm to 16 cm.

*Diameter*.—About 5 mm to 8 mm.

*Internode length*.—About 2 mm to 15 mm.

*Strength*.—Strong.

*Texture*.—Smooth, glabrous.

*Color*.—Close to 145C tinted with close to 187A.

Foliage description:

*Appearance*.—Leaves simple and asymmetrical; sessile.

*Length*.—About 6.9 cm to 11.4 cm.

*Width*.—About 1.7 cm to 2.7 cm.

*Shape*.—Elliptic.

*Apex*.—Acute.

*Base*.—Cuneate.

*Margin*.—Entire; moderately undulate.

*Texture, upper and lower surfaces*.—Smooth, glabrous.

*Venation pattern*.—Parallel.

*Color*.—Developing and fully expanded leaves, upper surface: Close to 137A; venation, close to 144B. Developing and fully expanded leaves, lower surface: Close to 137C; venation, close to 144A.

Flower description:

*Flower type and habit*.—Single cup-shaped flowers arranged in compound umbels; flowers face mostly outwardly; perianth segments separate; freely flowering habit with three to five flowers per inflorescence.

*Natural flowering season*.—Flowering continuous during the spring in The Netherlands; plants begin flowering about 80 to 90 days after planting.

*Fragrance*.—None detected.

*Flower longevity on the plant*.—About four weeks; flowers not persistent.

*Flower buds*.—Length: About 4 cm to 4.5 cm. Diameter: About 1.4 cm to 1.5 cm. Shape: Roughly ovoid. Color: Close to 53A.

*Umbel height*.—About 6 cm to 9 cm.

*Umbel diameter*.—About 12.5 cm to 14 cm.

*Flower diameter*.—About 6.5 cm to 7 cm.

*Flower depth*.—About 6.5 cm to 7 cm.

*Perianth*.—Arrangement: Six arranged in two whorls, each whorl with two lateral and one median segments. Inner perianth, lateral segments: Length: About 5.6 cm to 6.3 cm. Width: About 2.3 cm to 2.8 cm. Shape: Elliptic. Apex: Wishbone-shaped. Base: Attenuate. Margin: Entire; weakly undulate. Texture, upper and lower surfaces: Smooth, glabrous. Color, when opening and fully opened, upper surface: Towards the apex, close to 45B; center, close to 15C; towards the base, close to 47C; stripes, close to 183A. Color, when opening and fully opened, lower surface: Towards the apex, close to 45B; towards the base, close to 34C. Inner perianth, median segment: Length: About 4.2 cm to 5.5 cm. Width: About 2.2 cm to 2.6 cm. Shape: Elliptic. Apex: Wishbone. Base: Attenuate. Margin: Entire; weakly undulate. Texture, upper and lower surfaces: Smooth, glabrous. Color, when opening and fully opened, upper surface: Close to 45B; stripes, close to 183A. Color, when opening and fully opened, lower surface: Close to 45B. Outer perianth, lateral segments: Length: About 4.9 cm to 6 cm. Width: About 3.5 cm to 4.7 cm. Shape: Broadly obovate. Apex: Embedded pointed. Base: Attenuate. Margin: Entire; weakly undulate. Texture, upper and lower surfaces: Smooth, glabrous. Color, when opening and fully opened, upper surface: Close to 45B. Color, when opening and fully opened, lower surface: Close to 45B. Outer perianth, median segment: Length: About 5.1 cm to 5.7 cm. Width: About 3.6 cm to 4.3 cm. Shape: Broadly obovate. Apex: Embedded pointed. Base: Attenuate. Margin: Entire; weakly undulate. Texture, upper and lower surfaces: Smooth, glabrous. Color, when opening and fully opened, upper surface: Close to 45B. Color, when opening and fully opened, lower surface: Close to 45B.

*Pedicels*.—Length: About 5 mm to 2 cm. Diameter: About 1.5 mm to 2 mm. Strength: Strong. Angle: About 20° to 30° from vertical. Texture: Smooth, glabrous. Color: Close to 145C.

*Reproductive organs*.—Stamens: Quantity per flower: Six. Anther shape: Elliptic. Anther length: About 2 mm to 8 mm. Anther color: Upper surface: Close to 177A. Lower surface: Close to 176A. Pollen amount:

Scarce. Pollen color: Dark grey. Pistils: Quantity per flower: One. Style length: About 2.5 cm to 3 cm. Style color: Close to 46A. Stigma shape: Three-parted. Stigma color: Close to 53A. Ovary color: Close to 146B.

*Fruits and seeds*.—Fruit and seed development have not been observed on plants of the new *Alstroemeria*.

Disease & pest resistance: Plants of the new *Alstroemeria* have not been observed to be resistant to pathogens and pests common to *Alstroemeria* plants.

Garden performance: Plants of the new *Alstroemeria* have been observed to have excellent garden performance and to tolerate wind, rain and temperatures from about −5° C. to about 40° C.

It is claimed:

1. A new and distinct *Alstroemeria* plant named 'Zaprikate' as illustrated and described.

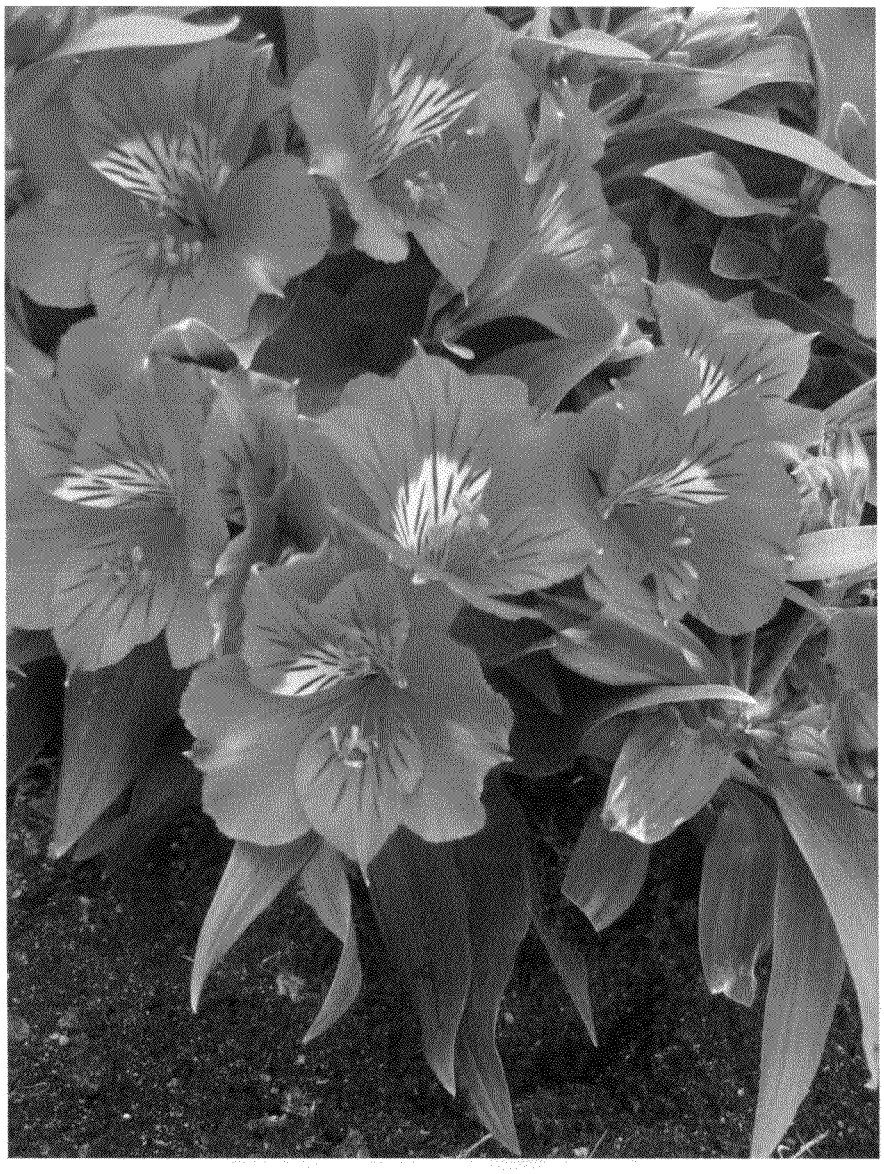

* * * * *